United States Patent [19]
Kovesdi et al.

[11] Patent Number: 5,994,106
[45] Date of Patent: *Nov. 30, 1999

[54] STOCKS OF RECOMBINANT, REPLICATION-DEFICIENT ADENOVIRUS FREE OF REPLICATION-COMPETENT ADENOVIRUS

[75] Inventors: Imre Kovesdi, Rockville; Douglas E. Brough, Olney; Duncan L. McVey, Derwood; Joseph T. Bruder, New Market; Alena Lizonova, Rockville, all of Md.

[73] Assignee: GenVec, Inc., Rockville, Md.

[ * ] Notice: This patent is subject to a terminal disclaimer.

[21] Appl. No.: 08/757,023

[22] Filed: Nov. 26, 1996

Related U.S. Application Data

[63] Continuation of application No. 08/258,416, Jun. 10, 1994.
[51] Int. Cl.$^6$ .............................. C12N 5/10; C12N 15/64; C12N 15/86
[52] U.S. Cl. ..................... 435/91.4; 435/320.1; 435/325; 435/366; 435/456
[58] Field of Search ................................. 435/69.1, 91.1, 435/172.1, 172.3, 375, 366, 320.1, 91.4, 455, 456, 325; 514/44; 424/199.1; 536/23.72, 24.1

[56] References Cited

U.S. PATENT DOCUMENTS

| | | | |
|---|---|---|---|
| 4,405,712 | 9/1983 | Vande Woude | 435/5 |
| 4,497,796 | 2/1985 | Salser et al. | 514/44 |
| 4,727,028 | 2/1988 | Santerre et al. | 435/356 |
| 4,740,463 | 4/1988 | Weinberg et al. | 435/456 |
| 5,190,931 | 3/1993 | Inouye | 435/91.32 |
| 5,208,149 | 5/1993 | Inouye | 435/252.3 |
| 5,518,913 | 5/1996 | Massie et al. | 435/235.1 |

FOREIGN PATENT DOCUMENTS

| | | |
|---|---|---|
| 94/68503 | 12/1994 | Australia . |
| 94/72646 | 1/1995 | Australia . |
| 95/28533 | 3/1996 | Australia . |
| 2053187 | 4/1993 | Canada . |
| 2117668 | 9/1995 | Canada . |
| 2707664 | 1/1995 | France . |
| WO 94/08026 | 4/1994 | WIPO . |
| WO 94/11506 | 5/1994 | WIPO . |
| WO 94/12649 | 6/1994 | WIPO . |
| WO 94/24297 | 10/1994 | WIPO . |
| WO 94/26914 | 11/1994 | WIPO . |
| WO 94/28152 | 12/1994 | WIPO . |
| WO 94/28938 | 12/1994 | WIPO . |
| WO 95/00655 | 1/1995 | WIPO . |
| WO 95/16772 | 6/1995 | WIPO . |
| WO 95/26411 | 10/1995 | WIPO . |
| WO 95/27071 | 10/1995 | WIPO . |
| WO 96/13596 | 5/1996 | WIPO . |
| WO 96/14061 | 5/1996 | WIPO . |
| WO 96/18418 | 6/1996 | WIPO . |

OTHER PUBLICATIONS

Armentano et al., *Human Gene Therapy*, 6, 1343–1353 (1995).
Berkner, *BioTechniques*, 6, 616–629 (1988).
Gilardi et al., *FEBS*, 267, 60–62 (1990).
Imler et al., *Gene Therapy*, 3, 75–84 (1996).
Mittereder et al., *Human Gene Therapy*, 5, 771–729 (1994).
Morin et al., *Molecular and Cellular Biology*, 4372–4380 (Oct. 1989).
Simon et al., *Human Gene Therapy*, 4, 771–780 (1993).
Yang et al., *Nature Genetics*, 7, 362–369 (1994).
T. Friedmann et al. Scientific American pp. 96–101, Jun. 1997.
S. Orkin et al. NIH Report on Gene Therapy, Dec. 1995.
R. Crystal Nature Medicine 1 (1) 15–17, 1995.
R. DeMatteo et al. Transplantation 63(2):315–9, 1997.
A. Schulick et al. J. Clin. Invest. 99(2) 209–19, 1997.
Q. Wang et al. Nature Medicine 2(6) 714–6, 1996.
Declaration of I. Koveschi, filed May 13, 1996 in 08/258, 416, 1996.
D. Davidson et al. J. Virology 61(4) 1226–39, 1987.
Brough et al., "A Gene Transfer Vector–Cell Line System for Complete Function Complementation of Adenovirus Early Regions E1 and E4," *J. Virol.*, 70(9), 6497–6501 (1996).
Engelhardt et al., "Ablation of E2A in Recombinant Adenoviruses Improves Transgene Persistance and Decrease Inflammatory Response in Mouse Liver," *Proc. Natl. Acad. Sci. USA*, 91, 6196–6200 (1994).
Zhou et al., "Progress Towards Development of an Adenoviral Vector with Deletions of E1 and E2a," *J. Cellular Biochemistry*, (supp. 21A), 434 (1995).
Barr et al., *Gene Therapy*, 1, 51–58 (1994).
Berkner et al., *Nucleic Acids Research*, 11 (17), 6003–6020 (1983).
Boucher et al., *Human Gene Therapy*, 5, 615–639 (1994).
Brough et al. *Virology*, 196, 269–281 (1993).
Brough et al., *Virology*, 190, 624–634 (1992).
Crystal et al., *Nature Genetics*, 8, 42–51 (Sep. 1994).
Englehardt et al., *Human Gene Therapy*, 4, 759–769 (1993).
Fallaux et al., *Human Gene Therapy*, 7, 215–222 (1996).
Graham et al., *J. Gen. Virol.*, 36, 59–72 (1977).
Klessig et al., *Molecular and Cellular Biology*, 4 (7), 1354–1362 (1984).
Kreeger, *The Scientist*, 13, (Feb. 19, 1996).
Krougliak et al., *Humans Gene Therapy*, 6, 1575–1586 (1995).

(List continued on next page.)

*Primary Examiner*—Scott D. Priebe
*Attorney, Agent, or Firm*—Leydig, Voit & Mayer, Ltd.

[57] ABSTRACT

The present invention provides multiply deficient adenoviral vectors and complementing cell lines. Also provided are recombinants of the multiply deficient adenoviral vectors and a therapeutic method, particularly relating to gene therapy, vaccination, and the like, involving the use of such recombinants.

24 Claims, 3 Drawing Sheets

OTHER PUBLICATIONS

Lemarchand et al., *PNAS USA*, 89, 6482–6486 (Jul. 1992).
Lemarchand et al., [*PNAS USA*, 89, 6482–6486 (Jul. 1992).]
Mastrangeli et al., *J. Clin. Invest.*, 91, 225–234 (Jan. 1993).
Rosenfeld et al., *Cell*, 68, 143–158 (1992).
Schaack et al., *J. Virol.*, 69, 4079–4085 (1995).
Trapnell et al., *Current Opinion in Biotechnology*, 5, 617–625 (1994).
Vos et al., *Virology*, 172, 634–642 (1989).
Wang et al., *Gene Therapy*, 2, 775–783 (1995).
Weinberg et al., *PNAS USA*, 80, 5383–86 (1983).
Yang et al., *PNAS USA*, 91, 4407–4411 (1994).
Yeh et al., *J. Virol.*, 70 (1), 559–565 (1996).

STOCKS OF RECOMBINANT, REPLICATION-DEFICIENT ADENOVIRUS FREE OF REPLICATION-COMPETENT ADENOVIRUS

This is a continuation of application Ser. No. 08/258,416, file on Jun. 10, 1994.

TECHNICAL FIELD OF THE INVENTION

The present invention relates to recombinant, multiply deficient adenoviral vectors and complementing cell lines and to the therapeutic use of such vectors.

BACKGROUND OF THE INVENTION

During the winter and spring of 1952–1953, Rowe and his colleagues at the National Institutes of Health (NIH) obtained and placed in tissue culture adenoids that had been surgically removed from young children in the Washington, D.C. area (Rowe et al., Proc. Soc. Exp. Biol: Med., 84, 570–573 (1953)). After periods of several weeks, many of the cultures began to show progressive degeneration characterized by destruction of epithelial cells. This cytopathic effect could be serially transmitted by filtered culture fluids to established tissue cultures of human cell lines. The cytopathic agent was called the "adenoid degenerating" (Ad) agent. The name "adenovirus" eventually became common for these agents. The discovery of many prototype strains of adenovirus, some of which caused respiratory illnesses, followed these initial discoveries (Rowe et al., supra; Dingle et al., Am. Rev. Respir. Dis., 97, 1–65 (1968); reviewed in Horwitz, "Adenoviridae and their replication," In Virology, Fields et al., eds., 2nd ed., Raven Press Ltd., New York, N.Y., pp. 1679–1721 (1990)).

Over 40 adenoviral subtypes have been isolated from humans and over 50 additional subtypes have been isolated from other mammals and birds (reviewed in Ishibashi et al., "Adenoviruses of animals," In The Adenoviruses, Ginsberg, ed., Plenum Press, New York, N.Y., pp. 497–562 (1984); Strauss, "Adenovirus infections in humans," In The Adenoviruses, Ginsberg, ed., Plenum Press, New York, N.Y., pp. 451–596 (1984)). All these subtypes belong to the family Adenoviridae, which is currently divided into two genera, namely Mastadenovirus and Aviadenovirus. All adenoviruses are morphologically and structurally similar. In humans, however, adenoviruses show diverging immunological properties and are, therefore, divided into serotypes. Two human serotypes of adenovirus, namely Ad2 and Ad5, have been studied intensively and have provided the majority of information about adenoviruses in general.

Adenoviruses are nonenveloped, regular icosahedrons, 65–80 nm in diameter, consisting of an external capsid and an internal core. The capsid is composed of 20 triangular surfaces or facets and 12 vertices (Horne et al., J. Mol. Biol., 1, 84–86 (1959)). The facets are comprised of hexons and the vertices are comprised of pentons. A fiber projects from each of the vertices. In addition to the hexons, pentons, and fibers, there are eight minor structural polypeptides, the exact positions of the majority of which are unclear. One minor polypeptide component, namely polypeptide IX, binds at positions where it can stabilize hexon-hexon contacts at what is referred to as the group-of-nine center of each facet (Furcinitti et al., EMBO, 8, 3563–3570 (1989)). The minor polypeptides VI and VIII are believed to stabilize hexon-hexon contacts between adjacent facets, and the minor polypeptide IIIA, which is known to be located in the regions of the vertices, is suggested to link the capsid and the core (Stewart et al., Cell, 67, 145–154 (1991)).

The viral core contains a linear, double-stranded DNA molecule with inverted terminal repeats (ITRs), which vary in length from 103 bp to 163 bp (Garon et al., PNAS USA 69, 2391–2394 (1972); Wolfson et al., PNAS USA, 69, 3054–3057 (1972); Arrand et al., J. Mol. Biol., 128, 577–594 (1973); Steenberg et al., Nucleic Acids Res., 4, 4371–4389 (1977); and Tooze, DNA Tumor Viruses, 2nd ed., Cold Spring Harbor, N.Y.: Cold Spring Harbor Laboratory. pp. 943–1054 (1981)). The ITRs harbor origins of DNA replication (Garon et al., supra; Wolfson et al., supra; Arrand et al., supra; Steenberg et al., supra). The viral DNA is associated with four polypeptides, namely V, VII, $\mu$, and terminal polypeptide (TP). The 55 kd TP is covalently linked to the 5' ends of the DNA via a dCMP (Rekosh et al., Cell, 11, 283–295 (1977); Robinson et al., Virology, 56, 54–69 (1973)). The other three polypeptides are noncovalently bound to the DNA and fold it in such a way as to fit it into the small volume of the capsid. The DNA appears to be packaged into a structure similar to cellular nucleosomes as seen from nuclease digestion patterns (Corden et al., PNAS USA, 73, 401–404 (1976); Tate et al., Nucleic Acids Res., 6, 2769–2785 (1979); Mirza et al., Biochim. Biophys. Acta, 696, 76–86 (1982)).

The overall organization of the adenoviral genome is conserved among serotypes, such that specific functions are similarly positioned. The Ad2 and Ad5 genomes have been completely sequenced and sequences of selected regions of genomes from other serotypes are available.

Adenovirus begins to infect a cell by attachment of the fiber to a specific receptor on the cell membrane (Londberg-Holm et al., J. Virol., 4, 323–338 (1969); Morgan et al., J. Virol., 4, 777–796 (1969); Pastan et al., "Adenovirus entry into cells: some new observations on an old problem," In Concepts in Viral Pathogenesis, Notkins et al., eds., Springer-Verlag, New York, N.Y., pp. 141–146 (1987)). Then, the penton base binds to an adenoviral integrin receptor. The receptor-bound virus then migrates from the plasma membrane to clathrin-coated pits that form endocytic vesicles or receptosomes, where the pH drops to 5.5 (Pastan et al., Concepts in Viral Pathogenesis, Notkins and Oldstone, eds. Springer-Verlag, N.Y. pp. 141–146 (1987)). The drop in pH is believed to alter the surface configuration of the virus, resulting in receptosome rupture and release of virus into the cytoplasm of the cell. The viral DNA is partially uncoated, i.e., partially freed of associated proteins, in the cytoplasm while being transported to the nucleus.

When the virus reaches the nuclear pores, the viral DNA enters the nucleus, leaving most of the remaining protein behind in the cytoplasm (Philipson et al., J. Virol., 2, 1064–1075 (1968)). However, the viral DNA is not completely protein-free—at least a portion of the viral DNA is associated with at least four viral polypeptides, namely V, VII, TP and $\mu$, and is converted into a viral DNA-cell histone complex (Tate et al., Nucleic Acids Res., 6, 2769–2785 (1979)).

The cycle from cell infection to production of viral particles lasts 1–2 days and results in the production of up to 10,000 infectious particles per cell (Green et al., Virology, 13, 169–176 (1961)). The infection process of adenovirus is divided into early (E) and late (L) phases, which are separated by viral DNA replication, although some events which take place during the early phase also take place during the late phase and vice versa. Further subdivisions have been made to fully describe the temporal expression of viral genes.

During the early phase, viral mRNA, which constitutes a minor proportion of the total RNA present in the cell, is synthesized from both strands of the adenoviral DNA present in the cell nucleus. At least five regions, designated E1–4 and MLP-L1, are transcribed (Lewis et al., *Cell,* 7, 141–151 (1976); Sharp et al., *Virology,* 75, 442–456 (1976); Sharp, "Adenovirus transcription," In *The Adenoviruses*, Ginsberg, ed., Plenum Press, New York, N.Y., pp. 173–204 (1984)). Each region has a distinct promoter(s) and is processed to generate multiple mRNA species, and, therefore, each region may be thought of as a gene family.

The products of the early (E) regions serve regulatory roles for the expression of other viral components, are involved in the general shut-off of cellular DNA replication and protein synthesis, and are required for viral DNA replication. The intricate series of events regulating early mRNA transcription begins with expression of immediate early regions E1A, L1 and the 13.5 kd gene (reviewed in Sharp (1984), supra; Horwitz (1990), supra). Expression of the delayed early regions E1B, E2A, E2B, E3 and E4 is dependent on the E1A gene products. Three promoters, the E2 promoter at 72 map units (mu), the protein IX promoter, and the IVa promoter are enhanced by the onset of DNA replication but are not dependent on it (Wilson et al., *Virology,* 94, 175–184 (1979)). Their expression characterizes an intermediate phase of viral gene expression. The result of the cascade of early gene expression is the start of viral DNA replication.

Adenoviral DNA replication displaces one parental single-strand by continuous synthesis in the 5' to 3' direction from replication origins at either end of the genome (reviewed in Kelly et al., "Initiation of viral DNA replication," In *Advances in Virus Research*, Maramorosch et al., eds., Academic Press, Inc., San Diego, Calif., 34: 1–42 (1988); Horwitz (1990), supra; van der Vliet, "Adenovirus DNA replication in vitro," In *The Eukaryotic Nucleus*, Strauss et al., eds., Telford Press, Caldwell, N.J. 1: 1–29 (1990)). Three viral proteins encoded from E2 are essential for adenoviral DNA synthesis: the single-stranded DNA binding protein (DBP), the adenoviral DNA polymerase (Ad pol), and the pre-terminal protein (pTP). In addition to these, in vitro experiments have identified many host cell factors necessary for DNA synthesis.

DNA synthesis is initiated by the covalent attachment of a dCMP molecule to a serine residue of pTP. The pTP-dCMP complex then functions as the primer for Ad pol to elongate. The displaced parental single-strand can form a panhandle structure by base-pairing of the inverted terminal repeats. This terminal duplex structure is identical to the ends of the parental genome and can serve as an origin for the initiation of complementary strand synthesis.

Initiation of viral DNA replication appears to be essential for entry into the late phase. The late phase of viral infection is characterized by the production of large amounts of the viral structural polypeptides and the nonstructural proteins involved in capsid assembly. The major late promoter (MLP) becomes fully active and produces transcripts that originate at 16.5 mu and terminate near the end of the genome. Post-transcriptional processing of this long transcript gives rise to five families of late mRNA, designated L1–5 (Shaw et al., *Cell,* 22, 905–916 (1980)). The mechanisms which control the shift from the early to late phase and result in such a dramatic shift in transcriptional utilization are unclear. The requirement for DNA replication may be a cis-property of the DNA template, since late transcription does not occur from a superinfecting virus at a time when late transcription of the primary infecting virus is active (Thomas et al., *Cell,* 22, 523–533 (1980)).

Assembly of the virion is an intricate process from the first step of assembling major structural units from individual polypeptide chains (reviewed in Philipson, "Adenovirus Assembly," In *The Adenoviruses*, Ginsberg, ed., Plenum Press, New York, N.Y. (1984), pp. 309–337; Horwitz (1990), supra). Hexon, penton base, and fiber assemble into trimeric homopolymer forms after synthesis in the cytoplasm. The 100 kd protein appears to function as a scaffolding protein for hexon trimerization and the resulting hexon trimer is called a hexon capsomere. The hexon capsomeres can self-assemble to form the shell of an empty capsid, and the penton base and fiber trimers can combine to form the penton when the components are inside the nucleus. The facet of the icosahedron is made up of three hexon capsomeres, which can be seen by dissociation of the capsid, but the intermediate step of formation of a group-of-nine hexons has not been observed. Several assembly intermediates have been shown from experiments with temperature-sensitive mutants. The progression of capsid assembly appears dependent on scaffolding proteins, 50 kd and 30 kd, and the naked DNA most probably enters the near-completed capsid through an opening at one of the vertices. The last step of the process involves the proteolytic trimming of the precursor polypeptides pVI, pVII, pVIII and pTP, which stabilizes the capsid structure, renders the DNA insensitive to nuclease treatment, and yields a mature virion.

Recombinant adenoviral vectors have been used in gene therapy. The use of a recombinant adenoviral vector to transfer one or more recombinant genes enables targeted delivery of the gene or genes to an organ, tissue, or cells in need of treatment, thereby overcoming the delivery problem encountered in most forms of somatic gene therapy. Furthermore, recombinant adenoviral vectors do not require host cell proliferation for expression of adenoviral proteins (Horwitz et al., *In Virology*, Raven Press, New York, 2, 1679–1721 (1990); and Berkner, *BioTechniques,* 6, 616 (1988)) and, if the diseased organ in need of treatment is the lung, has the added advantage of being normally trophic for the respiratory epithelium (Straus, In *Adenoviruses*, Plenum Press, New York, pp. 451–496 (1984)).

Other advantages of adenoviruses as potential vectors for human gene therapy are as follows: (i) recombination is rare; (ii) there are no known associations of human malignancies with adenoviral infections despite common human infection with adenoviruses; (iii) the adenoviral genome (which is linear, double-stranded DNA) currently can be manipulated to accommodate foreign genes ranging in size from small peptides up to 7.0–7.5 kb in length; (iv) an adenoviral vector does not insert its DNA into the chromosome of a cell, so its effect is impermanent and unlikely to interfere with the cell's normal function; (v) the adenovirus can infect non-dividing or terminally differentiated cells, such as cells in the brain and lungs; and (vi) live adenovirus, having as an essential characteristic the ability to replicate, has been safely used as a human vaccine (Horwitz, M. S. et al.; Berkner et al.; Straus et al.; Chanock et al., *JAMA,* 195, 151 (1966); Haj-Ahmad et al., *J. Virol.,* 57, 267 (1986); and Ballay et al., *EMBO,* 4, 3861 (1985)).

Until now, adenoviral vectors used to express a foreign gene have been deficient in only a single early region (E1) that is essential for viral growth, i.e., singly functionally deficient. Only the essential region E1 or, alternatively, the nonessential region E3 has been removed for insertion of a foreign gene into the adenoviral genome. If the region removed from the adenovirus is essential for the virus to grow, a complementing system, such as a complementing cell line is necessary to compensate for the missing viral function. In other words, the complementing cell line will express the missing viral function so that the singly deficient adenovirus can grow inside the complementing cell. Currently, there are only a few cell lines that exist that will complement for essential functions missing from a singly deficient adenovirus. Examples of such cell lines include HEK-293 (Graham et al., *Cold Spring Harbor Symp. Quant. Biol.*, 39, 637–650 (1975)), W162 (Weinberg et al., *PNAS USA*, 80, 5383–5386 (1983)), and gMDBP (Klessig et al., *Mol. Cell. Biol.*, 4, 1354–1362 (1984); Brough et al., *Virology*, 190, 624–634 (1992)).

Foreign genes have been inserted into two major regions of the adenoviral genome for use as expression vectors. Insertion into the E1 region results in defective progeny that require either growth in complementary cells or the presence of an intact helper virus (Berkner et al., *J. Virol.*, 61, 1213–1220 (1987); Davidson et al., *J. Virol.*, 61, 122–1239 (1987); and Mansour et al., *Mol. Cell Biol.*, 6, 2684–2694 (1986)). This region of the genome has been used most frequently for expression of foreign genes. Such E1-defective expression vector viruses usually have been grown in the HEK-293 cell line, which contains and expresses the complementing adenoviral E1 region. The inserted genes have been placed under the control of various promoters and most produce large amounts of the foreign gene product, dependent on the expression cassette. These adenoviral vectors, however, are defective in noncomplementing cell lines. In contrast, the E3 region is nonessential for virus growth in tissue culture, and replacement of this region with a foreign gene expression cassette leads to a virus that can productively grow in a noncomplementing cell line. The insertion and expression of the hepatitis B surface antigen in the E3 region with subsequent inoculation and formation of antibodies in the hamster has been reported (Morin et al., *PNAS USA*, 84, 4626–4630 (1987)).

The problem with singly deficient adenoviral vectors is that they limit the amount of usable space within the adenoviral genome for insertion and expression of a foreign gene. Due to similarities, or overlap, in the viral sequences contained within the singly deficient adenoviral vectors and the complementing cell lines that currently exist, recombination events can take place and create replication competent viruses within a vector stock. This event can render a stock of vector unusable for gene therapy purposes as a practical matter.

Accordingly, it is an object of the present invention to provide multiply deficient adenoviral vectors that can accommodate insertion and expression of larger pieces of foreign DNA. It is another object of the present invention to provide cell lines that complement the present inventive multiply deficient adenoviral vectors. It is also an object of the present invention to provide recombinants of multiply deficient adenoviral vectors and therapeutic methods, particularly relating to gene therapy, vaccination, and the like, involving the use of such recombinants. These and other objects and advantages of the present invention, as well as additional inventive features, will be apparent from the following detailed description.

BRIEF SUMMARY OF THE INVENTION

The present invention provides multiply deficient adenoviral vectors and complementing cell lines. The multiply deficient adenoviral vectors can accommodate insertion and expression of larger fragments of foreign DNA than is possible with currently available singly deficient adenoviral vectors. The multiply deficient adenoviral vectors are also replication deficient, which is particularly desirable for gene therapy and other therapeutic purposes. Accordingly, the present invention also provides recombinant multiply deficient adenoviral vectors and therapeutic methods, for example, relating to gene therapy, vaccination, and the like, involving the use of such recombinants.

DETAILED DESCRIPTION OF THE INVENTION

Figure 1:
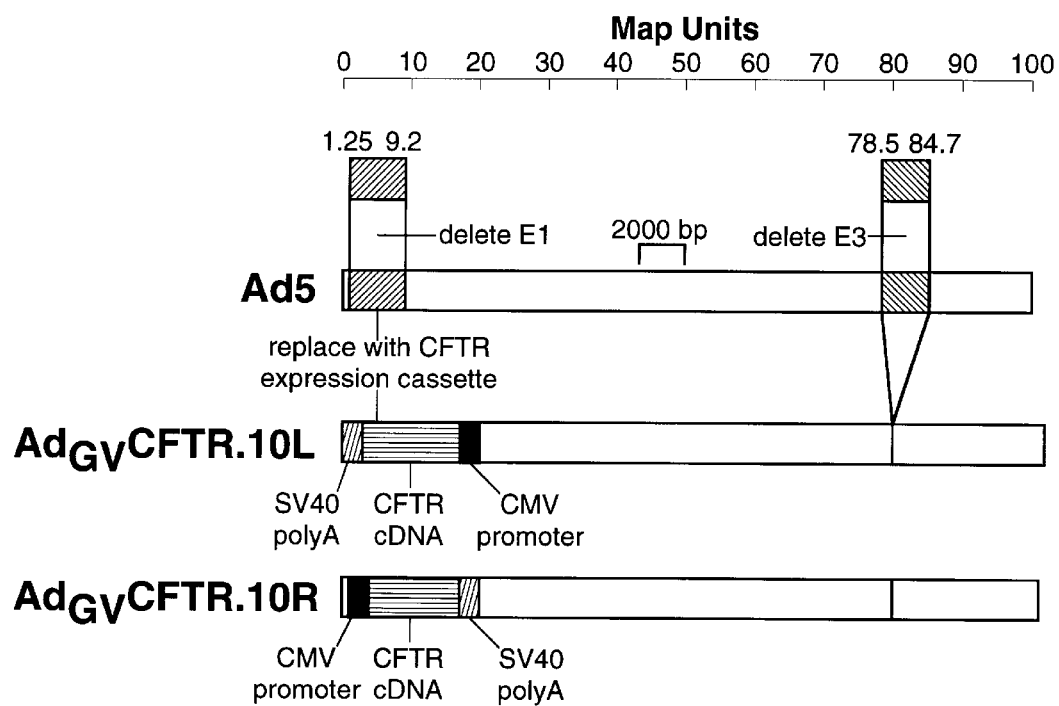
FIG. 1 is a set of schematic diagrams of the $Ad_{GV}CFTR.10L$ and $Ad_{GV}CFTR.10R$ viral vectors.

The present invention provides, among other things, multiply deficient adenoviral vectors for gene cloning and expression. The multiply deficient adenoviral vectors of the present invention differ from currently available singly deficient adenoviral vectors in being deficient in at least two essential gene functions and in being able to accept and express larger pieces of foreign DNA.

Any subtype, mixture of subtypes, or chimeric adenovirus may be used as the source of DNA for generation of the multiply deficient adenoviral vectors. However, given that the Ad5 genome has been completely sequenced, the present invention will be described with respect to the Ad5 serotype.

Preferably, the adenoviral vector of the present invention is at least deficient in a function provided by early region 1 (E1) and/or one or more functions encoded by early region 2 (E2), such as early region 2A (E2A) and early region 2B (E2B), and/or early region 3 (E3), and/or early region 4 (E4) of the adenoviral genome. Any one of the deleted functional regions then may be replaced with a promoter-variable expression cassette to produce a novel gene product. The insertion of a novel gene into the E2A region, for example, may be facilitated by the introduction of a unique restriction site, such that the novel gene product may be expressed from the E2A promoter.

The present invention, however, is not limited to adenoviral vectors that are deficient in gene functions only in the early region of the genome. Also included are adenoviral vectors that are deficient in the late region of the genome, adenoviral vectors that are deficient in the early and late regions of the genome, as well as vectors in which essentially the entire genome has been removed, in which case it is preferred that at least either the viral inverted terminal repeats and some of the promoters or the viral inverted terminal repeats and a packaging signal are left intact. One of ordinary skill in the art will appreciate that the larger the region of the adenoviral genome that is removed, the larger the piece of exogenous DNA that can be inserted into the genome. For example, given that the adenoviral genome is 36 kb, by leaving the viral inverted terminal repeats and some of the promoters intact, the theoretical capacity of the adenovirus is approximately 35 kb. Alternatively, one could generate a multiply deficient adenoviral vector that contains only the ITR and a packaging signal. This could then effectively allow for expression of 37–38 kb of foreign DNA from this vector.

In general, virus vector construction relies on the high level of recombination between fragments of adenoviral DNA in the cell. Two or three fragments of adenoviral DNA, containing regions of similarity (or overlap) between fragments and constituting the entire length of the genome, are transfected into a cell. The host cell's recombination machinery constructs a full-length viral vector genome. Similar procedures for constructing viruses containing alterations in various single regions have been previously described (Berkner et al., *Nucleic Acids Res.*, 12, 925–941 (1984); Berkner et al., *Nucleic Acids Res.*, 11, 6003–6020 (1983); Brough et al., *Virol.*, 190, 624–634 (1992)) and can be used to construct multiply deficient viruses as can in vitro recombination and ligation, for example.

The first step in virus vector construction is to construct a deletion or modification of a particular region of the adenoviral genome in a plasmid cassette using standard molecular biological techniques. After extensive analysis, this altered DNA (containing the deletion or modification) is then moved into a much larger plasmid that contains up to one half of the adenovirus genome. The next step is to transfect the plasmid DNA (containing the deletion or modification) and a large piece of the adenovirus genome into a recipient cell. Together these two pieces of DNA encompass all of the adenovirus genome plus a region of similarity. Within this region of similarity a recombination event will take place to generate a complete intact viral genome with the deletion or modification. In the case of multiply deficient vectors, the recipient cell will provide not only the recombination functions but also all missing viral functions not contained within the transfected viral genome. The multiply deficient vector can be further modified by alteration of the ITR and/or packaging signal, for example, such that the multiply deficient vector only functions in a complementing cell line.

In addition, the present invention also provides complementing cell lines for propagation of the present inventive multiply deficient adenoviral vectors. The preferred cell lines of the present invention are characterized in complementing for at least one gene function of the gene functions comprising the E1, E2, E3 and E4 regions of the adenoviral genome. Other cell lines include those that complement adenoviral vectors that are deficient in at least one gene function from the gene functions comprising the late regions, those that complement for a combination of early and late gene functions, and those that complement for all adenoviral functions. One of ordinary skill in the art will appreciate that the cell line of choice would be one that specifically complements for those functions that are missing from the recombinant multiply deficient adenoviral vector of interest and that can be generated using standard molecular biological techniques. The cell lines are further characterized in containing the complementing genes in a nonoverlapping fashion, which eliminates the possibility of the vector genome recombining with the cellular DNA. Accordingly, replication-competent adenoviruses are eliminated from the vector stocks, which are, therefore, suitable for certain therapeutic purposes, especially gene therapy purposes. This also eliminates the replication of the adenoviruses in noncomplementing cells.

The complementing cell line must be one that is capable of expressing the products of the two or more deficient adenoviral gene functions at the appropriate level for those products in order to generate a high titer stock of recombinant adenoviral vector. For example, it is necessary to express the E2A product, DBP, at stoichiometric levels, i.e., relatively high levels, for adenoviral DNA replication, but the E2B product, Ad pol, is necessary at only catalytic levels, i.e., relatively low levels, for adenoviral DNA replication. Not only must the level of the product be appropriate, the temporal expression of the product must be consistent with that seen in normal viral infection of a cell to assure a high titer stock of recombinant adenoviral vector. For example, the components necessary for viral DNA replication must be expressed before those necessary for virion assembly. In order to avoid cellular toxicity, which often accompanies high levels of expression of the viral products, and to regulate the temporal expression of the products, inducible promoter systems are used. For example, the sheep metallothionine inducible promoter system can be used to express the complete E4 region, the open reading frame 6 of the E4 region, and the E2A region. Other examples of suitable inducible promoter systems include, but are not limited to, the bacterial lac operon, the tetracycline operon, the T7 polymerase system, and combinations and chimeric constructs of eukaryotic and prokaryotic transcription factors, repressors and other components. Where the viral product to be expressed is highly toxic, it is desirable to use a bipartite inducible system, wherein the inducer is carried in a viral vector and the inducible product is carried within the chromatin of the complementing cell line. Repressible/inducible expression systems, such as the tetracycline expression system and lac expression system also may be used.

DNA that enters a small proportion of transfected cells can become stably maintained in an even smaller fraction. Isolation of a cell line that expresses one or more transfected genes is achieved by introduction into the same cell of a second gene (marker gene) that, for example, confers resistance to an antibiotic, drug or other compound. This selection is based on the fact that, in the presence of the antibiotic, drug, or other compound, the cell without the transferred gene will die, while the cell containing the transferred gene will survive. The surviving cells are then clonally isolated and expanded as individual cell lines. Within these cell lines are those that will express both the marker gene and the genes of interest. Propagation of the cells is dependent on the parental cell line and the method of selection. Transfection of the cell is also dependent on cell type. The most common techniques used for transfection are calcium phosphate precipitation, liposome, or DEAE dextran mediated DNA transfer.

Many modifications and variations of the present illustrative DNA sequences and plasmids are possible. For example, the degeneracy of the genetic code allows for the substitution of nucleotides throughout polypeptide coding regions, as well as in the translational stop signal, without alteration of the encoded polypeptide coding sequence. Such substitutable sequences can be deduced from the known amino acid or DNA sequence of a given gene and can be constructed by conventional synthetic or site-specific mutagenesis procedures. Synthetic DNA methods can be carried out in substantial accordance with the procedures of Itakura et al., *Science*, 198, 1056 (1977) and Crea et al., *PNAS USA*, 75, 5765 (1978). Site-specific mutagenesis procedures are described in Maniatis et al., *Molecular Cloning: A Laboratory Manual*, Cold Spring Harbor, N.Y. (2d ed. 1989). Therefore, the present invention is in no way limited to the DNA sequences and plasmids specifically exemplified. Exemplified vectors are for gene therapy of cystic fibrosis and, therefore, contain and express the CFTR gene but the vectors described are easily convertible to treat other potential diseases including, but not limited to, other chronic lung diseases, such as emphysema, asthma, adult respiratory distress syndrome, and chronic bronchitis, as well as cancer, coronary heart disease, etc. Accordingly, any gene or DNA sequence can be inserted into a multiply deficient adenoviral vector. The choice of gene or DNA sequence should be one that will achieve a therapeutic effect, for example, in the context of gene therapy, vaccination, and the like.

One skilled in the art will appreciate that suitable methods of administering a multiply deficient adenoviral vector of the present invention to an animal for therapeutic purposes, e.g., gene therapy, vaccination, and the like (see, for example, Rosenfeld et al., *Science*, 252, 431–434 (1991), Jaffe et al., *Clin. Res.*, 39(2), 302A (1991), Rosenfeld et al., *Clin. Res.*, 39(2), 311A (1991), Berkner, *BioTechniques*, 6, 616–629 (1988)), are available, and, although more than one route can be used to administer the vector, a particular route can provide a more immediate and more effective reaction than another route. Pharmaceutically acceptable excipients are also well-known to those who are skilled in the art, and are readily available. The choice of excipient will be determined in part by the particular method used to administer the composition. Accordingly, there is a wide variety of suitable formulations of the pharmaceutical composition of the present invention. The following formulations and methods are merely exemplary and are in no way limiting. However, oral, injectable and aerosol formulations are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active iningredient in an inert base, such as gelatin and glycerin, or sucrose and acacia, emulsions, gels, and the like containing, in addition to the active ingredient, such excipients as are known in the art.

The vectors of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the vectors employed in the present invention may be made into suppositories by mixing with a variety of bases such as emulsifying bases or water-soluble bases.

Formulations suitable for vaginal administration may be presented as pessaries, tampons, creams, gels, pastes, foams, or spray formulas containing, in addition to the active ingredient, such carriers as are known in the art to be appropriate.

The dose administered to an animal, particularly a human, in the context of the present invention will vary with the gene or other sequence of interest, the composition employed, the method of administration, and the particular site and organism being treated. The dose should be sufficient to effect a desirable response, e.g., therapeutic or immune response, within a desirable time frame.

The multiply deficient adenoviral vectors and complementing cell lines of the present invention also have utility in vitro. For example, they can be used to study adenoviral gene function and assembly.

The following examples further illustrate the present invention and, of course, should not be construed as in any way limiting its scope. Enzymes referred to in the examples are available, unless otherwise indicated, from Bethesda Research Laboratories (BRL), Gaithersburg, Md. 20877, New England Biolabs Inc. (NEB), Beverly, Mass. 01915, or Boehringer Mannheim Biochemicals (BMB), 7941 Castleway Drive, Indianapolis, Ind. 46250, and are used in substantial accordance with the manufacturer's recommendations. Many of the techniques employed herein are well known to those in the art. Molecular biology techniques are described in detail in laboratory manuals, such as Maniatis et al., *Molecular Cloning: A Laboratory Manual*, Cold Spring Harbor, N.Y. (2d ed. 1989) and *Current Protocols in Molecular Bioloqy* (Ausubel et al., eds. (1987)). One of ordinary skill in the art will recognize that alternate procedures can be substituted for various procedures presented below. Although the examples and figures relate to $Ad_{GV}.10$, $Ad_{GV}.11$, $Ad_{GV}.12$, and $Ad_{GV}.13$ which contain the cystic fibrosis transmembrane regulator gene (CFTR), namely $Ad_{GV}CFTR.10$, $Ad_{GV}CFTR.11$, $Ad_{GV}CFTR.12$, and $Ad_{GV}CFTR.13$, these vectors are not limited to expression of the CFTR gene and can be used to express other genes and DNA sequences. For example, therefore, the present invention encompasses such vectors comprising any foreign gene (e.g., for use in gene therapy), any DNA sequence capable of expressing in a mammal a polypeptide capable of eliciting an immune response to the polypeptide (e.g., for use in vaccination), and any DNA sequence capable of expressing in a mammal any other therapeutic agent (e.g., an antisense molecule, particularly an antisense molecule selected from the group consisting of MRNA and a synthetic oligonucleotide).

EXAMPLE 1

This example describes the generation of one embodiment involving $AD_{GV}.10$, namely $Ad_{GV}CFTR.10$.

$Ad_{GV}CFTR.10$ expresses the CFTR gene from the cytomegalovirus (CMV) early promoter. Two generations of this vector have been constructed and are designated $Ad_{GV}CFTR.10L$ and $Ad_{GV}CFTR.10$ R, dependent on the direction in which the CFTR expression cassette is placed in the E1 region in relation to the vector genome as shown in FIG. 1, which is a set of schematic diagrams of $Ad_{GV}CFTR.10L$ and $Ad_{GV}CFTR.10R$.

The CFTR expression cassette was constructed as follows. pRK5 (Genentech Inc., South San Francisco, Calif.) was digested with Kpn I (New England Biolabs (NEB), Beverly, Mass.), blunt-ended with Mung Bean nuclease (NEB), and an Xho I linker (NEB) was ligated in place of the Kpn I site. The resulting vector was named pRK5-Xho I. pRK5-Xho I was then digested with Sma I (NEB) and Hin dIII (NEB) and blunt-ended with Mung bean nuclease. A plasmid containing the CFTR gene, pBQ4.7 (Dr. Lap-Chee Tsui, Hospital for Sick Children, Toronto, Canada), was digested with Ava I (NEB) and Sac I (NEB) and blunt-ended with Mung bean nuclease. These two fragments were isolated and ligated together to produce pRK5-CFTR1, the CFTR expression cassette.

pRK5-CFTR1 was digested with Spe I (NEB) and Xho I and blunt-ended with Klenow (NEB). pAd60.454 (Dr. L. E. Babiss, The Rockefeller University, New York, N.Y.), which contains Ad5 sequences from 1–454/3325–5788, was digested with Bal II (NEB) and blunt-ended with Klenow. These two fragments were purified from vector sequences by low-melt agarose technique (Maniatis et al., *Molecular Cloning: a laboratory manual*, Cold Spring Harbor Laboratory, Cold Spring Harbor, N.Y.,2nd ed. (1989)) and ligated together to produce the left arm plasmids pGVCFTR.10L and pGVCFTR.10R.

The left arm plasmid from pGVCFTR.10L or pGVCFTR.10R was digested with Nhe I (NEB). The right arm of the virus was produced by digesting Ad5d1324 (Dr. Thomas E. Shenk, Princeton University, Princeton, N.J.) with Cla I (NEB). The two fragments, a small 918 bp fragment and a large approximately 32,800 bp fragment, were separated by sucrose gradient centrifugation (Maniatis et al., supra). The large fragment was mixed with the left arm plasmid fragments and transfected into 293 cells by standard calcium phosphate protocol (Graham et al., *Virology*, 52, 456 (1973)). The resulting recombinant viruses were plaque-purified on 293 cells, and viral stocks were established using standard virology techniques (e.g., Berkner et al., (1983) and (1984), supra).

EXAMPLE 2

This example describes the generation of $Ad_{GV}CFTR.11$.

$Ad_{GV}CFTR.11$ was constructed by means of a single in vivo recombination between 1-27082, i.e., the left arm, of $Ad_{GV}CFTR.10$ and a plasmid (pGV11A, pGV11B, pGV11C, or pGV11D; described in detail below) containing 21562–35935, i.e., the right arm, of Ad5 linearized with Bam HI (NEB) and Sal I (NEB) and into which the various E3 and E4 alterations as described below were introduced.

The left arm from $Ad_{GV}$ CFTR.10 was isolated on a concave 10–40% sucrose gradient, wherein +e,fra 1/+ee th of the total solution was 40%, after intact $Ad_{GV}CFTR.10$ was digested with Spe I (NEB) and Srf I (Stratagene, La. Jolla, Calif.) to yield the 1-27082 bp fragment.

The right arm was obtained by Bam HI-Sal I digestion of a modified pGEM vector (pGBS). pGBS was generated as follows. pGemI (Promega, Madison, Wis.) was digested with Eco RI and blunt-ended with Klenow, and a Sal I linker was ligated into the vector. The resulting DNA was then digested with Sal I and religated, thereby replacing the Eco RI site with a Sal I site and deleting the sequence between the two Sal I sites, to generate pGEMH/P/S, which was digested with Hin dIII and blunt-ended with Klenow, and a Bam HI linker was ligated into the vector to generate pGEMS/B. pGEMS/B was digested with Bam HI and Sal I and ligated with an ~14 kb Bam HI-Sal I fragment (21562–35935 from Ad5) from a pBR plasmid called p50–1000 (Dr. Paul Freimuth, Columbia University, N.Y.) to generate pGBS.

Three different versions of the right arm plasmid have been constructed in order to introduce into the adenoviral vector two Ad E3 gene products having anti-immunity and anti-inflammatory properties. The large E3 deletion in pGBSΔE30RF6, designated pGV11(0) (Example 7), was essentially replaced with three different versions of an expression cassette containing the Rous sarcoma viruslong terminal repeat (RSV-LTR) promoter driving expression of a bicistronic mRNA containing at the 5' end the Ad2 E3 19 kDa anti-immunity gene product and at the 3' end the Ad5 E3 14.7 kDa anti-inflammatory gene product. One additional virus was constructed by deleting the 19 kDa cDNA fragment by Bst BI (NEB) fragment deletion. This virus, designated $Ad_{GV}CFTR.11(D)$, contains the RSV-LTR promoter driving expression of a monocistronic mRNA containing only the E3 14.7 kDa anti-inflammatory gene product.

The Spe I (27082)—Nde I (31089) fragment from pGBSΔE3 (Example 5) was subcloned into pUC 19 by first cloning the Eco RI (27331)—Nde I (31089) fragment into identical sites in the pUC 19 polylinker. A Hin dIII (26328)—Eco RI (27331) fragment generated from pGBS was then cloned into the Eco RI site of this clone to generate pHNΔE3. Using appropriate primers, a PCR fragment with flanking Xba I sites was generated containing the RSV-LTR promoter, the Ad2 E3 19 kDa gene product, and the Ad5 E3 14.7 kDa gene product. The amplified fragment was digested with Xba I and subcloned into pUC 19 to generate pXA. After analysis of the Xba I fragment, the fragment was ligated into pHNΔE3 to generate pHNRA.

Using appropriate primers, two PCR fragments with flanking Bst BI sites were generated that encode internal ribosomal entry sites (IRES), which are known to enhance the translation of mRNAs that contain them (Jobling et al., *Nature*, 325, 622–625 (1987); Jang et al., *Genes and Development*, 4, 1560–1572 (1990)). One fragment (version B) contains a 34 bp IRES from the untranslated leader of the coat protein mRNA of alfalfa mosaic virus (AMV RNA 4 leader) (Jobling et al., supra). The other fragment (version C) contains a 570 bp IRES from the 5' nontranslated region of encephalomyocarditis virus (EMCV) mRNA (Jang et al., supra). Each Bst BI fragment from version B or C was cloned in place of the Bst BI fragment in pXA. The resulting plasmids, named pXB and pXC, respectively, were moved into pHNΔE3 to generate pHNRB and PHNRC, respectively, after sequence analysis of the Xba I fragments.

The Spe I (27082)—Nde I (31089) fragment from pGBSΔE30RF6 was replaced with the Spe I—Nde I fragments from PHNRA, PHNRB, pHNRC and PHNRD to generate pGV11A, pGV11B, pGV11C and pGV11D, respectively.

The pGBV plasmid DNA was linearized with Bam HI and Sal I and mixed with the purified left arm DNA fragment in varying concentrations to give about 20 μg total DNA, using salmon sperm or calf thymus DNA (Life Technologies, Gaithersburg, Mass.) to bring the amount of DNA to about 20 μg as needed. The mixed fragments were then transfected into 293 cells using standard calcium phosphate techniques (Graham et al., supra).

Five days after transfection, the cell monolayer was harvested by freeze-thawing three times. The resulting hybrid virus was titered onto 293 cells and isolated plaques were picked. The process of plaque isolation was repeated twice more to ensure a single recombinant virus existed in the initial plaque stock. The plaque isolate stock was then amplified to a large viral stock according to standard virology techniques as described in Burlseson et al., *Virology: a Laboratory Manua*, Academic Press Inc. (1992).

Figure 2:
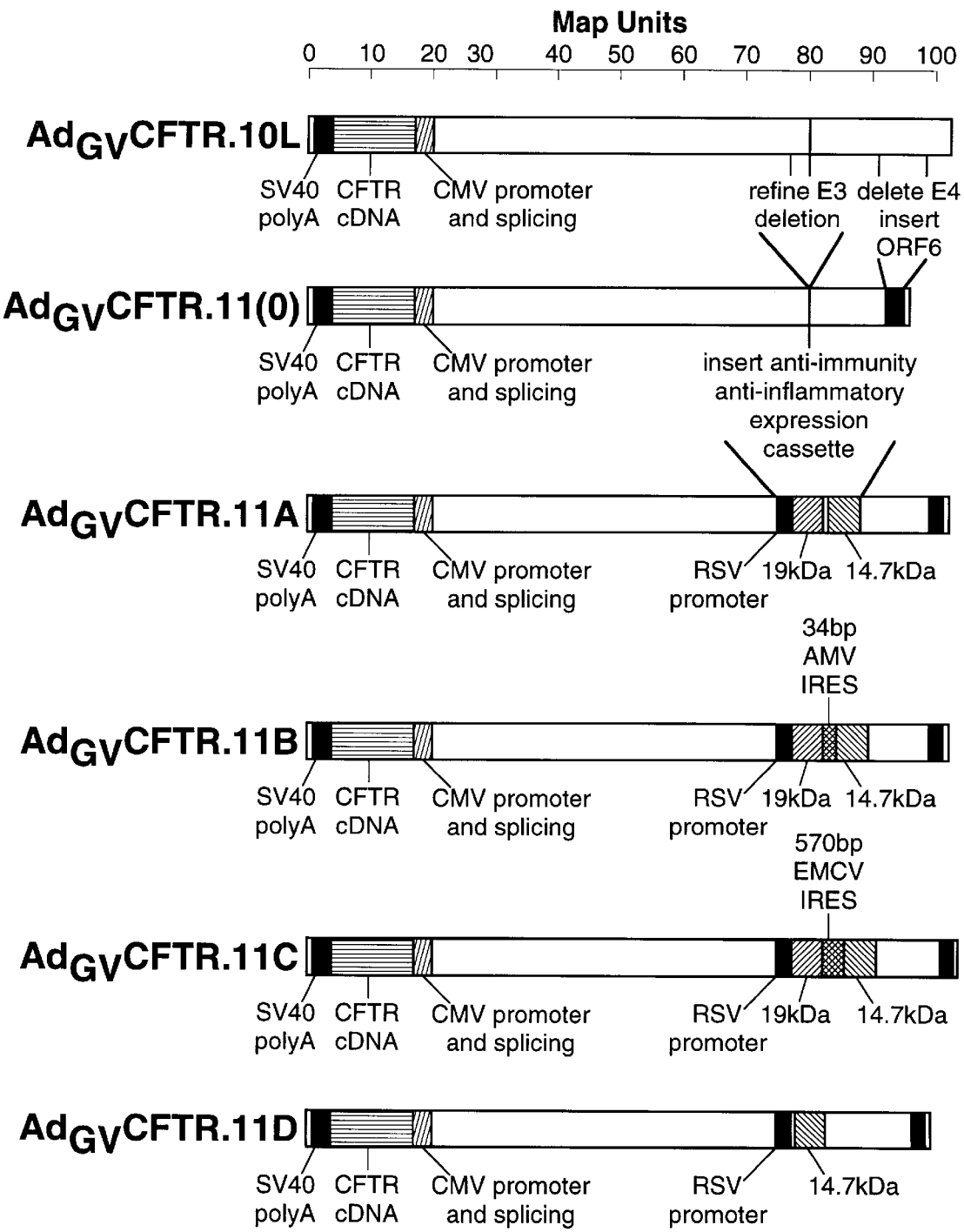
FIG. 2 is a set of schematic diagrams of the $Ad_{GV}CFTR.11$ viral vectors.
Figure 3:
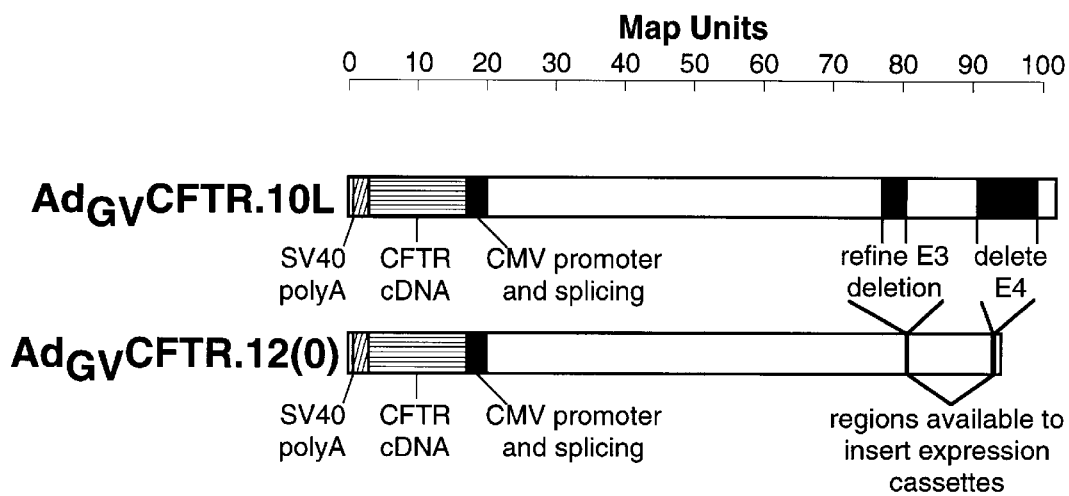
FIG. 3 is a schematic diagram of the $Ad_{GV}CFTR.12$ viral vector.
Figure 4:
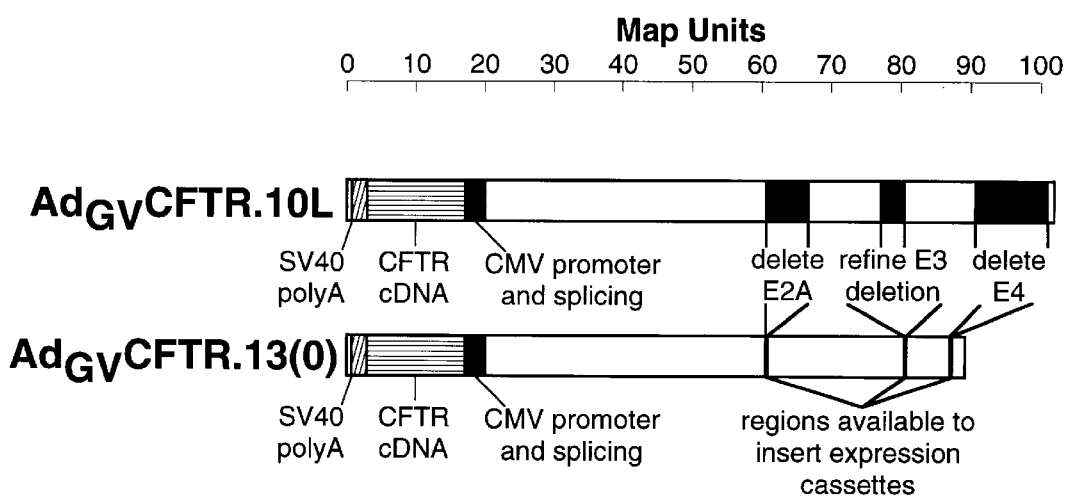
FIG. 4 is a schematic diagram of the $Ad_{GV}CFTR.13$ viral vector.

FIG. 2 is a set of schematic diagrams of the various $AD_{GV}CFTR.11$ viral vectors. The diagrams are aligned with that of $AD_{GV}CFTR.10L$ for comparison.

EXAMPLE 3

This example describes the generation of $Ad_{GV}CFTR.12$.

$Ad_{GV}.12$ is characterized by complete elimination of the E4 region. This large deletion allows for insertion of up to about 10 kb of exogenous DNA. More importantly, another region of the genome has become accessible for introduction of foreign gene expression cassettes. This deletion now enables the incorporation of larger expression cassettes for other products. For example, soluble receptors, i.e., TNF or IL-6 without a transmembrane domain so that they are now not attached to the membrane, and antisense molecules, e.g., those directed against cell cycle regulating products, such as cdc2, cdk kinases, cyclins, i.e., cyclin E or cyclin D, and transcription factors, i.e., E2F or c-myc, to eliminate inflammation and immune responses. pGV11 (O) is altered to produce a right arm plasmid in which the entire E4 region is deleted. The resulting plasmid in which the entire E3 and E4 regions are deleted is named pGV12(O). This is done by introducing a Pac I restriction site at the Afl III site at 32811 and the Bsg I site at 35640. Deletion of the Pac I fragment between these two sites effectively eliminates all of the E4 sequences including the E4 TATA element within the E4 promoter and the E4 poly A site.

Virus construction is performed as previously described except that the 293/E4 cell line or the 293/ORF6 cell line is used. The left arm from $Ad_{GV}CFTR.10L$, the right arm pGV12(O) plasmid, and all other general techniques are as described in Example 2. Since E4 contains essential gene products necessary for viral growth, the resulting E4 deletion mutant virus cannot grow in the absence of exogenously expressed E4. Therefore, all manipulations for viral construction are carried out in the new 293/E4 cell line or 293/ORF6 cell line (described in Examples 8 and 9, respectively). The resulting virus is $Ad_{GV}CFTR.12$.

EXAMPLE 4

This example describes the generation of $Ad_{GV}CFTR.13$.

$Ad_{GV}.13$ is characterized by not only complete elimination of E1, and E4 (as $Ad_{GV}.12$) but also complete elimination of E2A. The complete coding region of E2A is deleted by fusing together the DNA from two E2A mutant viruses, namely H5in800 and H5in804, containing insertions of Cla I restriction sites at both ends of the open reading frame (Vos et al., *Virology*, 172, 634–642 (1989); Brough et al., *Virology*, 190, 624–634 (1992)). The Cla I site of H5in800 is between codons 2 and 3 of the gene, and the Cla I site of H5in804 is within the stop codon of the E2A gene. The resultant virus contains an open reading frame consisting of 23 amino acids that have no similarity to the E2A reading frame. More importantly, this cassette offers yet another region of the virus genome into which a unique gene can be introduced. This can be done by inserting the gene of interest into the proper reading frame of the existing mini-ORF or by introducing yet another expression cassette containing its own promoter sequences, polyadenylation signals, and stop sequences in addition to the gene of interest.

Adenovirus DNA is prepared from H5in800 and H5in804. After digestion with the restriction enzyme Hin dIII (NEB), the Hin dIII A fragments from both H5in800 and H5in804 are cloned into pKS+(Stratagene). The resulting plasmids are named pKS+H5in800Hin dIIIA and pKS+H5in804Hin dIIIA, respectively. The Cla I (NEB) fragment from pKS+H5in800Hin dIIIA is then isolated and cloned in place of the identical Cla I fragment from PKS+H5in804Hin dIIIA. This chimeric plasmid, pHin dIIIAΔE2A effectively removes all of the E2A reading frame as described above. At this point, the E2A deletion is moved at Bam HI (NEB) and Spe I (NEB) restriction sites to replace the wild-type sequences in pGV12(O) to construct pGV13(O).

$Ad_{GV}CFTR.13$ virus is constructed as previously described by using $Ad_{GV}CFTR.10$ left arm DNA and pGV13 (O) right arm plasmid DNA. However, the recipient cell line for this virus construction is the triple complementing cell line 293/E4/E2A.

EXAMPLE 5

This example describes the generation of pGBSΔE3.

This plasmid was generated to remove the majority of the E3 region within pGBS, including the E3 promoter and existing E3 genes, to make room for other constructs and to facilitate introduction of E3 expression cassettes. This plasmid contains a deletion from 28331 to 30469.

A PCR fragment was generated with Ad5s(27324) and A5a(28330)X as primers and PGBS as template. The resulting fragment was digested with Eco RI (27331) and Xba I (28330) and gel-purified. This fragment was then introduced into pGBS at the Eco RI (27331) and Xba I (30470) sites.

EXAMPLE 6

This example describes the generation of pGBSΔE3ΔE4.

A large deletion of the Ad5E4 region was introduced into pGBSΔE3 to facilitate moving additional exogenous sequences into the adenoviral genome. The 32830–35566 E4 coding sequence was deleted.

A Pac I site was generated in place of the Mun I site at 32830 by treating PGBS Mun I-digested DNA with Klenow to blunt-end the fragment and by ligating a Pac I linker to this. The modified DNA was then digested with Nde I and the resulting 1736 bp fragment (Nde I 31089–Pac I 32830) was gel-purified. A PCR fragment was prepared using A5 (35564)P (IDT, Coralville, Ind.) and T7 primers (IDT, Coralville, Ind.) and PGBS as template. The resulting fragment was digested with Pac I and Sal I to generate Pac I 35566–Sal I 35935. A Sma I site within the polylinker region of pUC 19 was modified to a Pac I site by ligating in a Pac I linker. The Pac I 35566 Sal I 35935 fragment was moved into the modified pUC 19 vector at Pac I and Sal I sites, respectively, in the polylinker region. The modified Nde I 31089–Pac I 32830 fragment was moved into the pUC 19 plasmid, into which the Pac I 35566–Sal I 35935 fragment already had been inserted, at Nde I and Pac I sites, respectively. The Nde I 31089–Sal I 35935 fragment from the pUC 19 plasmid was purified by gel purification and cloned in place of the respective Nde I and Sal I sites in pGBSΔE3 to yield pGBSΔE3ΔE4.

EXAMPLE 7

This example describes the generation of pGBSΔE3ORF6.

The Ad5 894 bp E4 ORF-6 gene was placed 3' of the E4 promoter in pGBSΔE3 ΔE4. ORF-6 is the only absolutely essential E4 product necessary for virus growth in a nonE4 complementing cell line. Therefore, this product was re-introduced into the right arm plasmid (Example 2) under its own promoter control so that $Ad_{GV}CFTR.11$ virus can be propagated in 293 cells.

A PCR fragment was generated using A5s(33190)P (32 bp; 5'CACTTAATTAAACGCCTACATGGGGGTAGAGT3') (SEQ ID NO:1) and A5a(34084)P (34 bp;

5'CACTTAATTAAGGAAATATGACTACGTCCGGCGT3') (SEQ ID NO:2) as primers (IDT, Coralville, Ind.) and pGBS as template. This fragment was digested with Pac I and gel-purified. The product was introduced into the single Pac I site in pGBSΔE3ΔE4 to generate pGV11(O), which was the plasmid that was E3-modified for expression of the 19 kDa and 14.7 kDa Ad E3 products.

EXAMPLE 8

This example describes the generation of the 293/E4 cell line.

The vector pSMT/E4 was generated as follows. A 2752 bp Mun I (site 32825 of Ad2)—Sph I (polylinker) fragment was isolated from pE4 (89–99), which is a pUC19 plasmid into which was subcloned region 32264–35577 from Ad2, blunt-ended with Klenow, and treated with phosphatase (NEB). The 2752 bp Mun I-Sph I fragment was then ligated into pMTO10/A+ (McNeall et al., Gene, 76, 81–89 (1989)), which had been linearized with Bam HI, blunt-ended with Klenow and treated with phosphatase, to generate the expression cassette plasmid, pSMT/E4.

The cell line 293 (ATCC CRL 1573; American Type Culture Collection, Rockville, Md.) was cultured in 10% fetal bovine serum Dulbecco's modified Eagle's medium (Life Technologies, Gaithersburg, Mass.). The 293 cells were then transfected with pSMT/E4 linearized with Eco RI by the calcium phosphate method (Sambrook et al., *Molecular Cloning: a Laboratory Manual*, Cold Spring Harbor Laboratory Press (1989)). Approximately 24–48 hours post-transfection, medium (as above) containing 100 µM methotrexate and amethopterin (Sigma Chemical Co., St. Louis, Mo.) was added. The presence of methotrexate in the medium selects for expression of the dihydrofolate reductase (DHFR) gene, which is the selectable marker on the pSMT/E4 plasmid.

The normal cell DHFR gene is inhibited by a given concentration of methotrexate (cell type-specific), causing cell death. The expression of the additional DHFR gene in transfected cells containing pSMT/E4 provides resistance to methotrexate. Therefore, transfected cells containing the new genes are the only ones that grow under these conditions (for review, see Sambrook et al., supra).

When small colonies of cells formed from the initial single cell having the selectable marker, they were clonally isolated and propagated (for review, see Sambrook et al., supra). These clones were expanded to produce cell lines that were screened for expression of the product—in this case, E4—and screened for functionality in complementing defective viruses—in this case, both E1 and E4 defective viruses.

The result of this process produced the first 293/E4 cell lines capable of complementing adenoviral vectors defective in both E1 and E4 functions, such as $Ad_{GV}CFTR.12$.

EXAMPLE 9

This example describes the generation of the 293/ORF-6 cell line.

The primers A5s(33190)P and A5a(34084)P were used in a polymerase chain reaction (PCR) (*PCR Protocols. A guide to Methods and Applications*, Innis et al., eds., Academic Press, Inc. (1990)) to amplify the ORF-6 gene of Ad5 E4 and generate Pac I sites at the ends for cloning. The amplified fragment was blunt-ended with Klenow and cloned into pCR-Script SK(+) (Stratagene, La Jolla, Calif.). The resulting plasmid, pCR/ORF-6, was sequenced and then the ORF-06 insert was transferred into the pSMT/puro expression vector, which was generated by ligation of a blunt-ended Eco RI—Hin dIII fragment containing the SMT promoter into the blunt-ended Mlu I-Hin dIII site in pRCpuro, to generate pSMT/ORF-6.

The 293 cell line was cultured and transfected with pSMT/ORF-6 as described in Example 8, except that the transfected cells were placed under selection for the puromycin resistance gene, which allows cells that express it to grow in the presence of puromycin. Colonies of transformed cells were subcloned and propagated and were screened as described in Example 8.

This cell line is suitable for complementing vectors that are deficient in the E1 and E4 regions, such as the $Ad_{GV}CFTR.12$ series of vectors.

EXAMPLE 10

This example describes the generation of the 293/E4/E2A cell line. The 293/E4/E2A cell line allows E1, E4 and E2A defective viral vectors to grow.

The E2A expression cassette for introduction into 293/E4 cells is produced as follows. The first step is to alter surrounding bases of the ATG of E2A to make a perfect Kozak consensus (Kozak, *J. Molec. Biol.*, 196, 947–950 (1987)) to optimize expression of E2A. Two primers are designed to alter the 5' region of the E2A gene. Ad5s(23884), an 18 bp oligonucleotide (5'GCCGCCTCATCCGCTTTT3') (SEQ ID NO:3), is designed to prime the internal region flanking the Sma I site of the E2A gene. DBP(ATG)R1, a 32-bp gonucleotide (5'CCGGAATTCCACCATGGCGAGtcGGAAGG3') (SEQ ID NO:4), is designed to introduce the translational consensus sequence around the ATG of the E2A gene modifying it into a perfect Kozak extended consensus sequence and to introduce an Eco RI site just 5' to facilitate cloning. The resulting PCR product using the above primers is digested with Eco RI and Sma I (NEB) and cloned into the idetical polylinker sites of pBluescript IIKS+(Stratagene, La Jolla, Calif.). The resulting plasmid is named pKS/ESDBP.

A Sma I-Xba I fragment is isolated from pHRKauffman (Morin et al., *Mol. Cell. Biol.*, 9, 4372–4380 (1989)) and cloned into the corresponding Sma I and Xba I sites of pKS/ESDBP to complete the E2A reading frame. The resulting plasmid is named pKSDBP. In order to eliminate all homologous sequences from vector contained within the expression cassette, the Kpn I to Dra I fragment from pKSDBP is moved into corresponding Kpn I and Pme I sites in PNEB193 (NEB) in which the Eco RI sites in the polylinker have been destroyed (GenVec). The resulting clone, pE2A, contains all of the E2A reading frame without any extra sequences homologous to the E2A deleted vector in Example 4.

A 5' splice cassette is then moved into pE2A to allow proper nuclear processing of the mRNA and to further enhance expression of E2A. To do this, pRK5, described in Example 1, is digested with Sac II (NEB), blunt-ended with Mung Bean nuclease (NEB), and digested with Eco RI (NEB). The resulting approx. 240 bp fragment of interest containing the splicing signals is cloned into the Cla I (blunt-ended with Klenow) to Eco RI sites of pE2A to generate p5'E2A. The blunt-ended (Klenow) Sal I to Hin dIII fragment from p5'E2A containing the E2A sequences is moved into the blunt-ended (Klenow) Xba I site of pSMT/puro and pSMT/neo. The resulting E2A is named pKSE2A.

The Xba I fragment from pKSE2A that contained all the E2A gene is moved into the Xba I site of pSMT/puro and pSMT/neo. The resulting E2A expression plasmids, pSMT/ E2A/puro and pSMT/E2A/neo, are transfected into 293/E4 and 203/ORF-6 cells, respectively. Cells transfected with pSMT/E2A/puro are selected for growth in standard media plus puromycin and cells transfected with pSMT/E2A/neo are selected for growth in standard media plus G418. Clonal expansion of isolated colonies is as described in Example 8. The resulting cell lines are screened for their ability to complement E1, E4 and E2A defective viral vectors.

These cell lines are suitable for complementing vectors that are deficient in the E1, E4 and E2A regions of the virus, such as those described in the $Ad_{GV}CFTR.13$ series of viral vectors.

EXAMPLE 11

This example describes the generation of complementing cell lines using the cell line A549 (ATCC) as the parental line.

Ad2 virus DNA is prepared by techniques previously described. The genomic DNA is digested with Ssp I and Xho I and the 5438 bp fragment is purified and cloned into Eco RV/Xho I sites of pKS+(Stratagene) to produce pKS341- 5778. After diagnostic determination of the clone, an Xho I (blunt-ended with Klenow) to Eco RI fragment is moved into Nru I (blunt) to Eco RI sites in pRC/CMVneo to produce pE1neo. Transformation of A549 cells with this clone yields a complementing cell line (similar to 293), wherein additional expression cassettes can be introduced, in a manner similar to that described for the 293 cell, to produce multicomplementing cell lines with excellent plaqueing potential.

All references, including publications and patents, cited herein are hereby incorporated by reference to the same extent as if each reference were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

What is claimed is:

1. A replication-competent adenovirus-free stock of a recombinant adenoviral vector, wherein said adenoviral vector is deficient in one or more essential gene functions of one or more regions of the adenoviral genome selected from the group consisting of the E1, E2A, and E4 regions of the adenoviral genome.

2. The stock of claim 1, wherein said adenoviral vector is deficient in one or more essential gene functions of E1.

3. The stock of claim 1, wherein said adenoviral vector is deficient in one or more essential gene functions of E2A.

4. The stock of claim 1, wherein said adenoviral vector is deficient in one or more essential gene functions of E4.

5. The stock of claim 1, wherein said adenoviral vector is deficient in two or more essential gene functions.

6. The stock of claim 5, wherein said adenoviral vector is deficient in one or more essential gene functions of each of the E1 and E2A regions of the adenoviral genome.

7. The stock of claim 5, wherein said adenoviral vector is deficient in one or more essential gene functions of each of the E1 and E4 regions of the adenoviral genome.

8. The stock of claim 5, wherein said adenoviral vector is deficient in one or more essential gene functions of each of the E2A and E4 regions of the adenoviral genome.

9. The stock of claim 1, wherein said adenoviral vector is deficient in three essential gene functions.

10. The stock of claim 9, wherein said adenoviral vector is deficient in one or more essential gene functions of each of the E1, E2A, and E4 regions of the adenoviral genome.

11. The stock of claim 1, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

12. The stock of claim 2, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

13. The stock of claim 3, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

14. The stock of claim 4, wherein said adenoviral vector is prepared in a cell that complements in trans the deficient essential gene functions of said vector, wherein the genome of said cell line is free of overlapping sequences with said vector that are sufficient to mediate a recombination event resulting in a replication competent adenoviral vector.

15. The stock of claim 5, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

16. The stock of claim 6, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

17. The stock of claim 7, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

18. The stock of claim 8, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

19. The stock of claim 9, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

20. The stock of claim 10, wherein said adenoviral vector is prepared in a cell that complements in trans the deficient essential gene functions of said adenoviral vector, wherein the genome of said cell line is free of overlapping sequences with said adenoviral vector that are sufficient to mediate a recombination event resulting in a replication competent adenoviral vector.

21. A system comprising (i) a cell having a cellular genome comprising at least one DNA sequence, which is operably linked to an inducible promoter or a repressible promoter, and which complements in trans for a deficiency in one or more essential gene functions of the E1 and E2A regions of an adenoviral genome, and (ii) an adenoviral vector comprising an adenoviral genome having a deficiency in one or more essential gene functions of the E1 and E2A regions of said adenoviral genome, wherein there is insufficient overlap between said cellular genorne and said adenoviral genome to mediate a recombination event sufficient to result in a replication-competent adenovirus.

22. A system comprising (i) a cell having a cellular genome comprising at least one DNA sequence, which is operably linked to an inducible promoter or a repressible promoter, and which complements in trans for a deficiency in one or more essential gene functions of the E1, E2A and E4 regions of an adenoviral genome, and (ii) an adenoviral vector comprising an adenoviral genome having a deficiency in one or more essential gene functions of the E1, E2A and E4 regions of said adenoviral genome, wherein there is insufficient overlap between said cellular genome and said adenoviral genome to mediate a recombination event sufficient to result in a replication-competent adenovirus.

23. A method of propagating an adenoviral vector that is deficient in one or more essential gene functions of one or more regions of an adenoviral genome, which method comprises propagating an adenoviral vector comprising an adenoviral genome having a deficiency in one or more essential gene functions of the E1 and E2A regions in a cell having a cellular genome comprising at least one DNA sequence that complements in trans said deficiency, wherein there is insufficient overlap between said cellular genome and said adenoviral genome to mediate a recombination event resulting in a replication-competent adenoviral vector.

24. A method of propagating an adenoviral vector that is deficient in one or more essential gene functions of one or more regions of an adenoviral genome, which method comprises propagating an adenoviral vector comprising an adenoviral genome having a deficiency in one or more essential gene finctions of the E1, E2A and E4 regions in a cell having a cellular genome comprising at least one DNA sequence that complements in trans said deficiency, wherein there is insufficient overlap between said cellular genome and said adenoviral genome to mediate a recombination event resulting in a replication-competent adenoviral vector.

* * * * *

```
                          SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 32 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:1:

CACTTAATTA AACGCCTACA TGGGGGTAGA GT                                       32

(2) INFORMATION FOR SEQ ID NO:2:

(i) SEQUENCE CHARACTERISTICS:
          (A) LENGTH: 34 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:2:

CACTTAATTA AGGAAATATG ACTACGTCCG GCGT                                     34

(2) INFORMATION FOR SEQ ID NO:3:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (ii) MOLECULE TYPE: DNA (synthetic)

(xi) SEQUENCE DESCRIPTION: SEQ ID NO:3:
```

-continued

```
GCCGCCTCAT CCGCTTTT                                                         18

(2) INFORMATION FOR SEQ ID NO:4:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:4:

CCGGAATTCC ACCATGGCGA GTCGGGAAGA GG                                         32
```